United States Patent [19]

Portman, Jr. et al.

[11] Patent Number: 4,697,657

[45] Date of Patent: Oct. 6, 1987

[54] PIEZOELECTRIC WEIGHING DEVICE

[76] Inventors: Joe L. Portman, Jr., 1423 Escalon, San Antonio, Tex. 78221; David J. Margraf, 1492 Cloud La., New Braunfels, Tex. 78130

[21] Appl. No.: 931,660

[22] Filed: Nov. 17, 1986

Related U.S. Application Data

[63] Continuation-in-part of Ser. No. 789,515, Oct. 21, 1985, Pat. No. 4,623,030.

[51] Int. Cl.⁴ .................... G01G 3/14; G01G 19/00; H01L 41/04
[52] U.S. Cl. ................................ 177/210 FP; 177/1; 177/25; 177/245; 364/568; 310/321
[58] Field of Search .................... 177/1, 25, 132, 144, 177/210 R, 210 FP, 245; 364/567, 568; 310/321

[56] References Cited

U.S. PATENT DOCUMENTS

| | | | |
|---|---|---|---|
| 3,814,914 | 6/1974 | List et al. | 235/151.1 |
| 3,926,271 | 12/1975 | Patashnick | 177/210 |
| 3,973,636 | 8/1976 | Uchida | 177/132 |
| 4,165,633 | 8/1979 | Raisanen | 73/76 |
| 4,168,623 | 9/1979 | Thomas, Jr. | 73/76 |
| 4,316,384 | 2/1982 | Pommer et al. | 73/76 |
| 4,544,858 | 10/1985 | Nishiguchi et al. | 310/321 |

*Primary Examiner*—George H. Miller, Jr.
*Attorney, Agent, or Firm*—Jack V. Musgrove

[57] ABSTRACT

A piezoelectric device is used to determine the absolute weight of an unknown sample by comparison to a control sample whose weight is known. A piezoelectric driver is resiliently attached to a base that is isolated from vibrations. A piezoelectric receiver and a reed are resiliently attached to the piezoelectric driver so that (1) the reed is moved in response to motion of the piezoelectric driver, and (2) the piezoelectric receiver gives an electric signal out proportional to motion of the system. The entire system is set to operate on the leading edge of the resonant frequency for the system. By applying an oscillating sine wave voltage, such as 140 hertz, to the piezoelectric driver, and by applying a known mass to the tip of the reed, a first output is obtained from the piezoelectric receiver which represents the calibrated weight. Next by exchanging an unknown sample for the known mass, a second output is obtained that represents the second weight. By a ratio of the second output/first output (or a signal equivalent to the weights being measured), the absolute weight of the unknown sample is determined.

41 Claims, 8 Drawing Figures

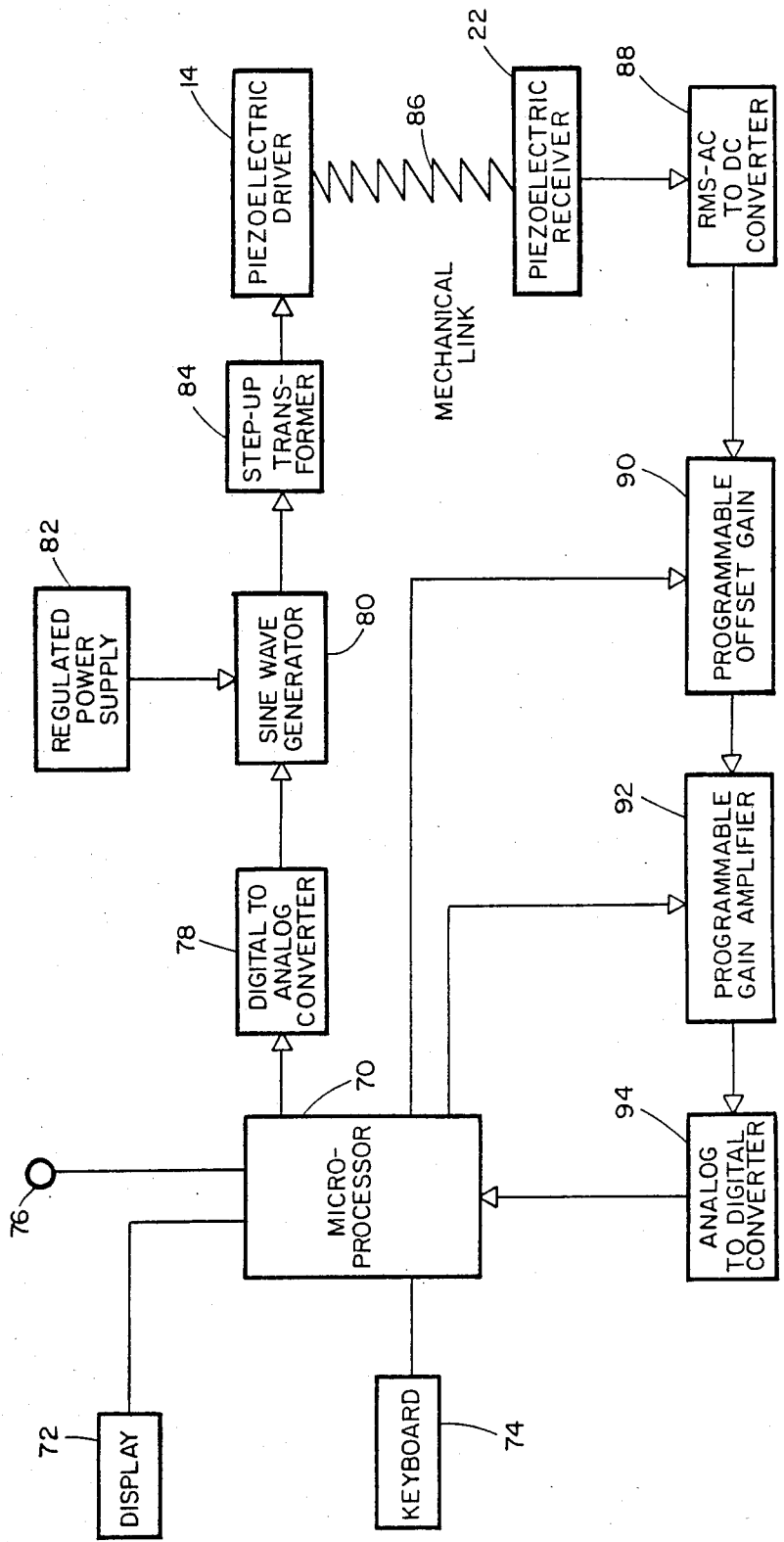

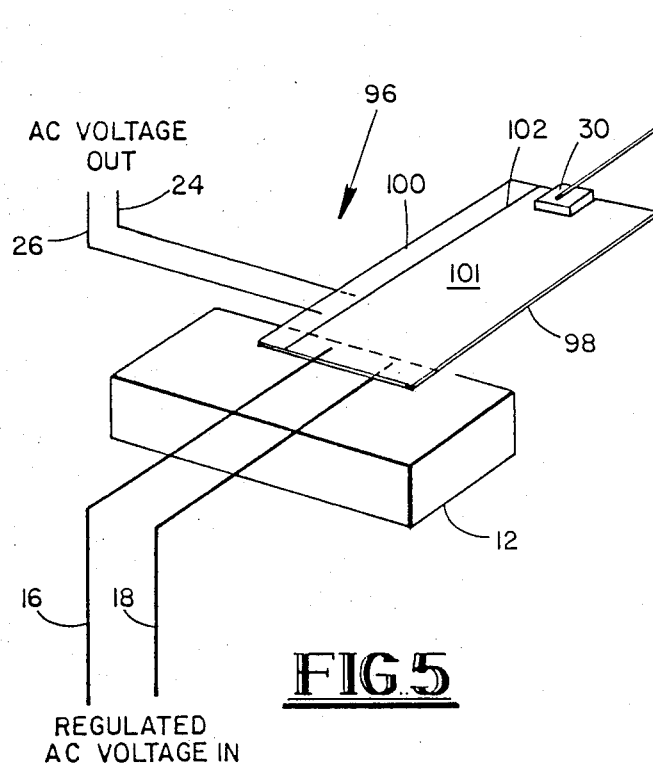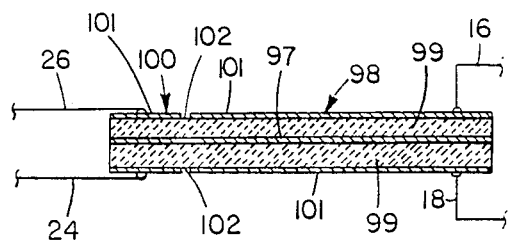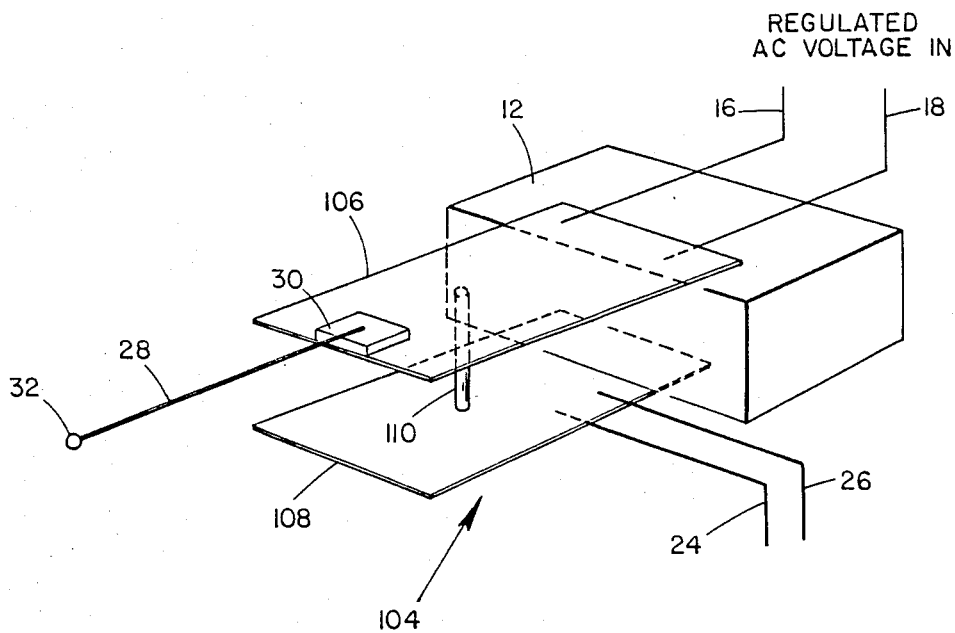

4,697,657

PIEZOELECTRIC WEIGHING DEVICE

CROSS-REFERENCES TO RELATED APPLICATIONS

The present invention is a continuation-in-part of U.S. patent application Ser. No. 789,515, for a Piezoelectric Ratio Weighing Device, filed Oct. 21, 1985 (now U.S. Pat. No. 4,623,030).

BACKGROUND OF THE INVENTION

1. Field of the Invention

The present invention relates to weighing devices and, more particularly, to a piezoelectric device that determines the actual weight of a given sample.

2. Brief Description of the Prior Art

Applicant's Assignee is in the business of determining the amount of carbon residue in petroleum-based materials. During processing of petroleum products, engineers want to know as expeditiously as possible the amount of high-boiling components in the petroleum products being processed. The lighter carbon products (such as gasoline, kerosene, and oil) have very small amounts of carbon residue. These products, which are sometimes referred to as "light" petroleum products, will quickly boil off if the temperature of the substance being processed is raised to approximately 500° C. However, the heavier petroleum products having larger, more complicated molecules would remain. This material is often referred to as carbon residue and may resemble tar. If the amount of carbon residue during the manufacturing process is too great, the manufacturer has one of two alternatives; namely, either use the carbon residue for low-profit items, such as the making of asphalt, or further processing the carbon residue in an attempt to "crack" the carbon residue molecules into lighter products. Sometimes the cracking is very expensive and costly. The processor of petroleum products wants to know as expeditiously as possible the amount of carbon residue that is in the petroleum product being processed so that the processor can make a decision on what additional processing steps, if any, need to be taken.

In the past, it has required a considerable length of time and laboratory work to determine the amount of carbon residue in a petroleum-base product. The most common method used in determining carbon residue was referred to as the Conradson Carbon Residue Test. This entailed the weighing of a sample, heating the sample until the light particles evaporate, and subsequently measuring the weight of the residue. This would give both weights from which a percent of carbon residue could be determined. These methods used in the Conradson Carbon Residue Test would normally take a couple of hours of laboratory time and would not give any type of instantaneous result so that the manufacturing process of petroleum-based products could be rapidly changed.

Various types of alternatives to the Conradson Carbon Residue Test have been developed, such as those described in an article by F. Noel entitled "An Alternative to the Conradson Carbon Residue Test", which is incorporated herein by reference. Mr. Noel uses a carbon residue test which uses extremely small samples to determine the amount of carbon residue. The present invention is an apparatus that can be used in measuring the extremely small sample sizes suggested by Mr. Noel.

In the field of weights and measures, it is extremely difficult to accurately weigh a small sample size. Dust, vibrations, wind, humidity or breath of the person making the measurements could affect the weight measurement. The parent application was directed towards the use of vibrating piezoelectric devices that may give a ratio of weights, but never actually know the quantity of the weights being measured. The present application is directed towards use of the same device to determine absolute weights, which is easily accomplished through calibration techniques. The piezoelectric device may have a driver element and, by measurements being taken from a receiver element, a signal proportional to the weight of the substance being measured is obtained.

In the past, piezoelectric ceramics have been commonly used in the industry to create resonant frequencies. The piezoelectric ceramic may act as either a receiver or driver. A good descriptive article entitled "Piezoelectric Ceramics" by Eric A. Kolm, et al. published in *Mechanical Engineering,* February 1984, p. 43, explains the operation of piezoelectric devices.

Many different types of weighing devices have been designed in the past that will eliminate vibrations and weigh small amounts, such as those shown in U.S. Pat. No. 4,088,014 to Wirth; U.S. Pat. No. 3,967,497 to Brown; U.S. Pat. No. 1,974,940 to Wood; U.S. Pat. No. 3,133,606 to Thomson; U.S. Pat. No. 3,680,650 to Zimmerer; U.S. Pat. No. 994,733 to Feinstein; and U.S. Pat. No. 633,471 to McGarvey. Other types of vibrating string weighing devices are shown in the prior art, such as illustrated by U.S. Pat. No. 3,701,392 to Wirth. However, Wirth simply stresses the vibrating mechanism itself. Another type of vibrating string mechanism that uses magnets is shown in U.S. Pat. No. 4,383,585 to Gauss.

However, none of the patents referred to hereinabove in any way suggest a piezoelectric type of device being used to determine the absolute weight of a small sample size using a system wherein the piezoelectric crystal is the driver and the receiver. Further, none of the prior art discloses any type of on-line system for a petrochemical processing plant whereby the amount of carbon residue can be monitored on an essentially continuous basis during the manufacturing process. An on-line device for determining carbon residue must be suitable for operation in the adverse environment of a petrochemical plant without requiring an undue amount of special consideration.

SUMMARY OF THE INVENTION

It is an object of the present invention to provide a piezoelectric apparatus that will accurately weigh small sample sizes.

It is another object of the present invention to provide a device for determining the amount of carbon residue in petrochemical product.

It is still another object of the present invention to provide a piczoelectric device that has a piezoelectric driver that vibrates in response to an AC signal, a piczoelectric receiver that gives an output signal in response to the vibrations, and a reed that vibrates when the piezoelectric driver vibrates. A sample applied to the tip of the reed will produce a signal, which can then be equated to weight through calibration means.

It is yet another object of the present invention to provide a piezoelectric device for determining such weights during a manufacturing process. A base with a fairly strong resilient member eliminates low-frequency vibrations. The base is connected to a first end of piezoelectric driver that is driven by an AC signal which causes the second end of the piezoelectric driver to vibrate. Attached to the second end of the piezoelectric driver is a piezoelectric receiver that vibrates therewith. The piezoelectric receiver gives an output signal that is representative of the vibration therein caused by the piezoelectric driver. A reed (that may be of the quartz or similar type) is attached on a first end to either the piezoelectric receiver or piezoelectric driver and vibrates therewith. The entire system operates on the leading edge of the resonant frequency for the system. In operation, first the system is run at zero level with no added weight. Then by applying a known weight sample to a ball tip on a second end of the reed, the entire system begins to operate closer to the resonant frequency. This will give a calibrated output reading from the piezoelectric receiver. This will give a calibrated output reading from the piezoelectric receiver. Thereafter, switching the control weight with the sample of unknown weight, a different mass remains on the end of the quartz reed. A second differential signal is recorded which can be compared with the first differential signal to give a ratio of the amount of material present. Given the known weight of the control mass, an absolute measurement may then be determined for the sample. The process may also be reversed. The sample may be placed on the ball tip yielding a first signal. Thereafter, the control weight may be placed on the ball, yielding the second differential signal.

To operate in a petrochemical processing plant, the entire device may be fully automated to give essentially continuous control. The piezoelectric weighing device would be mounted and calibrated entirely within a closed container with only a tip of the reed extending therefrom. In such a manner, a computer can then accurately control the temperature and humidity around the piezoelectric weighing device. The computer would also actuate a sampling valve that would allow a drop of fluid to be measured to splash against the tip of the reed extending from the box. By setting the entire piezoelectric weighing device at the leading edge of the resonant frequency, the added weight applied to the tip of the reed would shift the resonant frequency and cause the piezoelectric device to operate on the forward slope of the resonant frequency curve. Simultaneously, the computer can control an inert gas, such as nitrogen, that will flow over the tip of the reed to keep outside influences from interfering with the sample being measured by the piezoelectric device.

As a word of explanation, the surface tension of the petroleum-base product will be sufficient to maintain a relatively fixed sample on the tip of the reed after the first few vibrations. Even the continued vibrating motion would not cause the sample to fall from the tip of the reed because of the high surface tension.

After a first measurement has been taken from the piezoelectric receiver that is proportionate to the weight of the sample, heat is then applied to the tip of the reed. Typically, the computer may deliver nitrogen heated to approximately 500° C. to the tip of the reed. This would cause light carbon particles to evaporate leaving only the heavier carbon resins. In a typical example, 70 to 80% of the sample deposited on the tip of the reed would evaporate. The remaining 20 to 30% is then measured by a proportionate output signal from the piezoelectric receiver. By comparing the first output signal and the second output signal with the calibrated signal, the percent of the total sample deposited on the tip of the reed which is a carbon residue has been determined, as well as the actual weight thereof.

To clean the tip of the reed, the source of nitrogen is cut off by the computer and oxygen-enriched air heated to high temperatures of 500° C. or greater is delivered to the tip of the reed. The heated oxygen-enriched air simply oxidizes any remaining portions of the carbon residue. Thereafter, the process can be repeated.

The process as described hereinabove can be connected in-line in a petrochemical plant with the present invention periodically taking samples and within a minute or so determining the amount of carbon residue in the sample. By knowing the carbon residue in the sample, adjustments can be made during the processing of the petrochemical for a more efficient process. All of this can be very accurately controlled by a microprocessor programmed to control the piezoelectric weighing device.

It should be realized that the piezoelectric weighing device may take any number of particular embodiments with the piezoelectric receiver and piezoelectric driver being connected in parallel or series connection. All that is required is the piezoelectric driver drive; the piezoelectric receiver and the reed operate on the leading edge of resonant frequency of the system prior to the applying of a sample. In an alternative embodiment, the reed may be fixed at both ends, having the sample placed near the middle thereof.

To automate an in-line system, a computer control can include a microprocessor with some type of visual display and communication system. The microprocessor through a digital-to-analog converter would generate a sine wave typically in the range of 120–140 Hertz. Through a step-up transformer, a piezoelectric driver will begin to vibrate, which, in turn, vibrates the reed and the piezoelectric receiver. The signal from the piezoelectric receiver is converted to a DC voltage and fed through a programmable offset gain and a programmable gain amplifier, converted to digital and fed back to the microprocessor. By a feedback loop, the programmable offset gain provides the By a feedback loop, the programmable offset gain provides the zero point for the measurement at the leading edge of the resonant frequency for the system. The programmable gain amplifier also by a feedback loop provides the slope or the span of measurement to insure measurements are taken on the front side of the resonant frequency curve. For example, assume that the system would measure between 0–10 milligrams. This would be set by the programmable gain amplifier.

Internally within the microprocessor, the microprocessor would linearize the signal. This can be done by comparing to a chart for the known signal for the particular device or by a linearization equation. The linearization may have to be determined for each particular device as it is manufactured; however, if the manufacturing techniques are uniform enough, the method of linearization for one device may apply to all.

BRIEF DESCRIPTION OF THE DRAWINGS

FIG. 4 provides a block diagram representation of part of the computer control illustrated in FIG. 3.

FIG. 5 is a perspective view of an alternative piezoelectric weight measuring device.

FIG. 6 is a cross-sectional view of the piezoelectric receiver and piezoelectric driver shown in FIG. 5.

FIG. 7 is a perspective view of another alternative piezoelectric weight measuring device.

DESCRIPTION OF THE PREFERRED EMBODIMENTS

Petroleum products normally have very complicated and heavy molecules that form either coke or tar. If the percent of the heavy molecules is too great, the heavy molecules will damage the distillation towers, heat exchangers, or reactors in the normal petrochemical plant. Even if the heavy molecules do not cause physical damage, the heavy molecules will interfere with normal manufacturing processes causing higher maintenance, lower profit margins, and poorer quality products. These heavy molecules are the main components of carbon residue and are used in the forming of asphalt materials. However, a certain amount of carbon residue can be accommodated in the typical petrochemical processing plant so it becomes necessary to know the percent of carbon residue within the petrochemical being processed. By knowing the percent, the operators of the plant can use that percent as a guide for blending or further processing.

If the percent of carbon residue is too high, the processor at the plant may attempt to "crack" some of the heavy molecules by any of a number of ways, such as adding temperature, pressure, hydrogen, etc. If the heavy molecules are cracked, they will form much lighter and smaller molecules to form other petrochemical products, such as butane, propane, gasoline, etc. Petrochemical products such as butane and propane are not as heavy and therefore have a low carbon residue. For example, one typical molecule having high carbon residue could form a large number of molecules of butane. By knowing the percent of carbon residue in the product being processed, the operator can tell what needs to be done in the processing cycle. The determining of the percentage of the carbon residue in the petrochemical being processed is simply a tool that simplifies the overall processing of petrochemicals.

One of the big problems with determining the amount of carbon residue under present technology is that it is very time consuming. For example, a sample of the petrochemical being processed will have to be taken to the laboratory and a carbon residue test that takes approximately two hours would have to be run. By use of the present invention, the present carbon residue tester could be connected in-line at the refinery with the carbon residue being determined in a minute or two. This provides almost instantaneous feedback as to the carbon residue of the petrochemical being processed.

In the present invention, it was determined that a piezoelectric type device could be used to determine the weight of the carbon residue in a small sample. The smaller the sample, the quicker the carbon residue can be determined because the lighter materials must be heat separated from the carbon residue.

Figure 1:
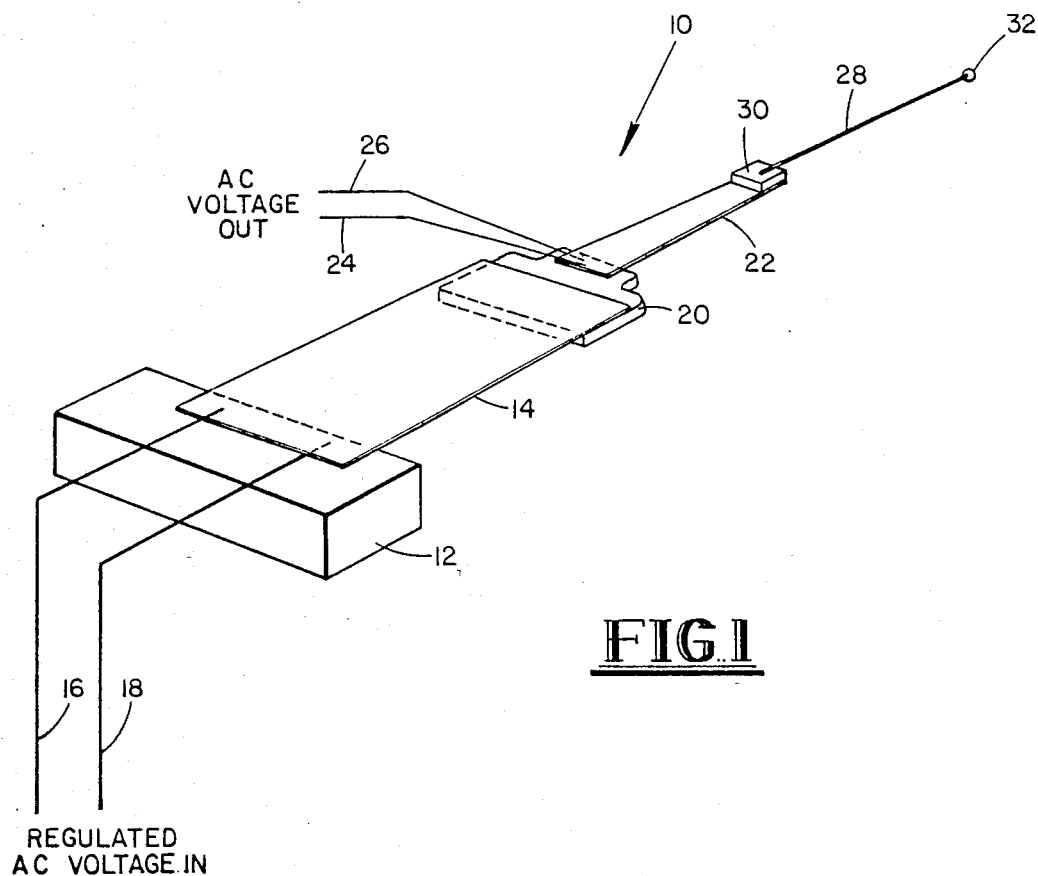
FIG. 1 is a perspective view of a piezoelectric weight measuring device.

Referring to FIG. 1, a simplified piezoelectric weighing device is illustrated generally by reference numeral 10. The piezoelectric weighing device has a base 12 which is the largest mass in the system. A piezoelectric driver 14 is attached to the base 12 by a suitable bonding material (not shown). The bonding material should be nonconductive so there will be no electrical conduction between the piezoelectric driver 14 and the base 12. A regulated AC voltage IN is connected to each side of the piezoelectric driver 14 by input lines 16 and 18 as shown.

With one end of the piezoelectric driver 14 being connected to the base 12, the opposite end of the piezoelectric driver 14 is bonded to a suitable dielectric material 20. Also connected to the dielectric material 20 is one end of a piezoelectric receiver 22. The piezoelectric receiver 22 has output lines 24 and 26 to give an AC voltage OUT during operation. Electrical isolation between piezoelectric driver 14 and piezoelectric receiver 22 is provided by dielectric material 20.

The opposite end of the piezoelectric receiver 22 is bonded to, but electrically isolated, from a reed 28 by a suitable dielectric material 30. The reed 28 can be of any particular material, but applicant has found that a quartz reed having a ball tip 32 on the end thereof is particularly suited for the present invention.

By applying a regulated AC voltage IN to the piezoelectric driver 14, the piezoelectric driver 14 will begin to vibrate thereby causing the dielectric material 20 and the piezoelectric receiver 22 attached thereto to also vibrate. The bending action of the piezoelectric receiver 22 generates an AC voltage OUT over output lines 24 and 26. The vibration of the piezoelectric receiver 22 will, in turn, cause the reed 28 to vibrate.

A basic physics formula to describe the natural resonance of a vibrating system is:

$$\frac{1}{f} = t = 2\pi \sqrt{\frac{m}{k}}$$

where,
 f is the frequency,
 t is the time period of simple harmonic motion,
 m is the mass,
 k is the modulus of elasticity.

This formula describes the natural frequency of the reed in the piezoelectric weighing device 10. It is important to see that only the reed 28, not the entire device, exhibits simple harmonic motion. Since k is fixed for the reed 28 being used, mass is the only variable in the formula. Increased mass yields a lower frequency, but this means the frequency of resonance is lower, not that the frequency itslef lowers. The frequency is the same, but the frequency vs. amplitude curve shifts because the amplitude (not part of the equation) increases.

Now at the start, the AC voltage OUT is zero, or is considered the starting AC Voltage OUT with zero weight applied. In either event, the AC voltage OUT is the reference point to which further AC voltage OUT will be compared. By placing a control sample of known weight on the ball 32 of the reed 28, the resonant frequency of the overall piezoelectric weighing device 10 is changed. Therefore, a first AC voltage OUT is given, with the variation between the starting AC voltage OUT being proportional to the mass of material on the ball tip 32 of the reed 28.

Next by removing the control weight and placing a second sample on the ball tip 32 of the reed 28, a second AC voltage OUT can be obtained, the variation between the starting AC voltage OUT and the second AC voltage OUT obtained, representing the mass then present. By comparing the first and second AC voltages OUT, a percent ratio of the mass remaining is determined, and then it is a simple step to calculate the weight of the subject sample.

Figure 2:
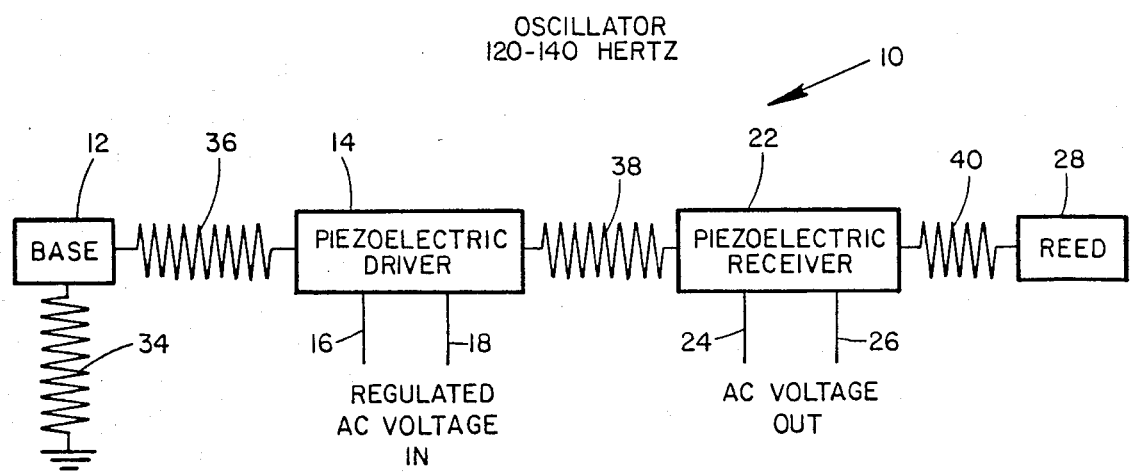
FIG. 2 is a schematic block representation of the piezoelectric weight measuring device illustrated in FIG. 1.

The piezoelectric weighing device 10 as illustrated in FIG. 1 is shown in a schematic block form in FIG. 2. The mass of base 12 is much larger than the mass of the piezoelectric driver 14, piezoelectric receiver 22, and reed 28. The spring 34 between the base 12 and the ground is fairly strong and eliminates low frequency vibrations. The natural frequency of the base 12 is very low in comparison to the normal operating frequency range of the piezoelectric weighing device 10. The base 12 and spring 34 is designed to eliminate external shock and vibration.

The piezoelectric driver 14 induces the entire system to vibrate. By adjusting the frequency of the regulated AC voltage IN, the resonant frequency of the device 14 is determined. Thereafter, the frequency is decreased slightly to insure that the device is operating on the leading edge of the resonant frequency if no sample is applied to ball tip 32. The springs 36 and 38 on either side of the piezoelectric driver 14 are about equal and much weaker than the spring 34 attaching base 12 to the ground. The regulated AC voltage IN through input lines 16 and 18 causes an oscillation of the piezoelectric driver 14 of between 120–140 hertz. By experimentation, it has been determined that the frequency range between 120–140 hertz is where the resonant frequency normally occurred in the test models. It is important that the normal operating frequency range of the piezoelectric weighing device 10 not include the natural frequency of the piezoelectric driver 14 operating alone.

As the piezoelectric driver 14 vibrates and its vibrations are transmitted through spring 38 to the piezoelectric receiver 22, piezoelectric receiver 22 will give an AC voltage OUT through output lines 24 and 26 as a result of the mechanical tension/compression that takes place during the vibration. The AC voltage OUT may be processed and interpolated by a computer depending upon the weight attached thereto. The natural frequency of the piezoelectric receiver 22 must not be included in the normal operating frequency range of the entire piezoelectric weighing device 10 for proper operation.

The reed 28 is the focal point of obtaining signals that are representative of weights. The reed 28 is connected by a very weak spring 40 to the piezoelectric receiver 22. Reed 28 may altenatively be fixed at both ends, one end being attached to piezoelectric driver 14. In this case, the mass to be weighed may be placed near the middle of reed 28. The piezoelectric driver 14 sets the entire piezoelectric weighing device 10 into vibratory motion at a frequency rate slightly lower than the resonant frequency of the device 10. A predetermined AC voltage OUT can be used for this setting, which predetermined AC voltage OUT would set the device 10 on the leading edge of the resonant frequency. The resonant frequency is determined by adjusting the frequency of the regulated AC voltage IN to give the maximum AC voltage OUT.

When weight is applied to the ball tip 32 of the reed 28 (such as splashing a drop of petrochemical solution thereon), the natural frequency of the reed 28 is decreased which provides an altered natural frequency for the entire piezoelectric weighing device 10. The altered natural frequency is now almost the same as the frequency of the regulated AC voltage IN except the regulated AC voltage IN is on the leading edge of the resonant frequency curve. This causes the reed 28 to approach full resonant condition where the reed 28 now exerts more tension and compression force on the piezoelectric receiver 22 because of the additional weight applied to reed 28.

Applying the piezoelectric weighing device 10 as previously described in connection with FIGS. 1 and 2 to a petroleum processing plant, a very small sample of the petrochemical being processed (for example, one drop) can be applied to the ball tip 32 of the reed 28. Through initial vibrations, some of this sample may even sling off the ball tip 32 of the reed 28. However, after initially slinging off any excess, the surface tension of the petrochemical product will cause the remaining part to cling to the ball tip 32 of the reed 28. This increased weight on the reed 28 will cause the entire piezoelectric weighing device 10 to resonate because it is operating on the leading edge of the device's resonant frequency. This causes an increased AC voltage OUT over output lines 24 and 26. This voltage may be equated to a first weight by previous calibration.

Next by heating the ball tip 32 to approximately 500° C., the lighter particles of the petrochemical being processed are boiled OFF or evaporate leaving the carbon residue. The carbon residue causes a different AC voltage OUT over output lines 24 and 26 that is representative of the weight remaining on the ball tip 32. By comparing the weight of the petroleum fluid to the absolute weight of the remaining mass, the ratio of the weight of the carbon residue to the petrochemical being processed is determined. This ratio by weight of the carbon residue is very important in the processing of petrochemicals.

Thereafter, the ball tip 32 of reed 28 may be cleaned by supplying oxygen at a high temperature to the ball tip 32 to essentially burn off the carbon residue thereby returning the piezoclectric weighing device 10 to its original zero state for measuring of another sample.

Figure 3:
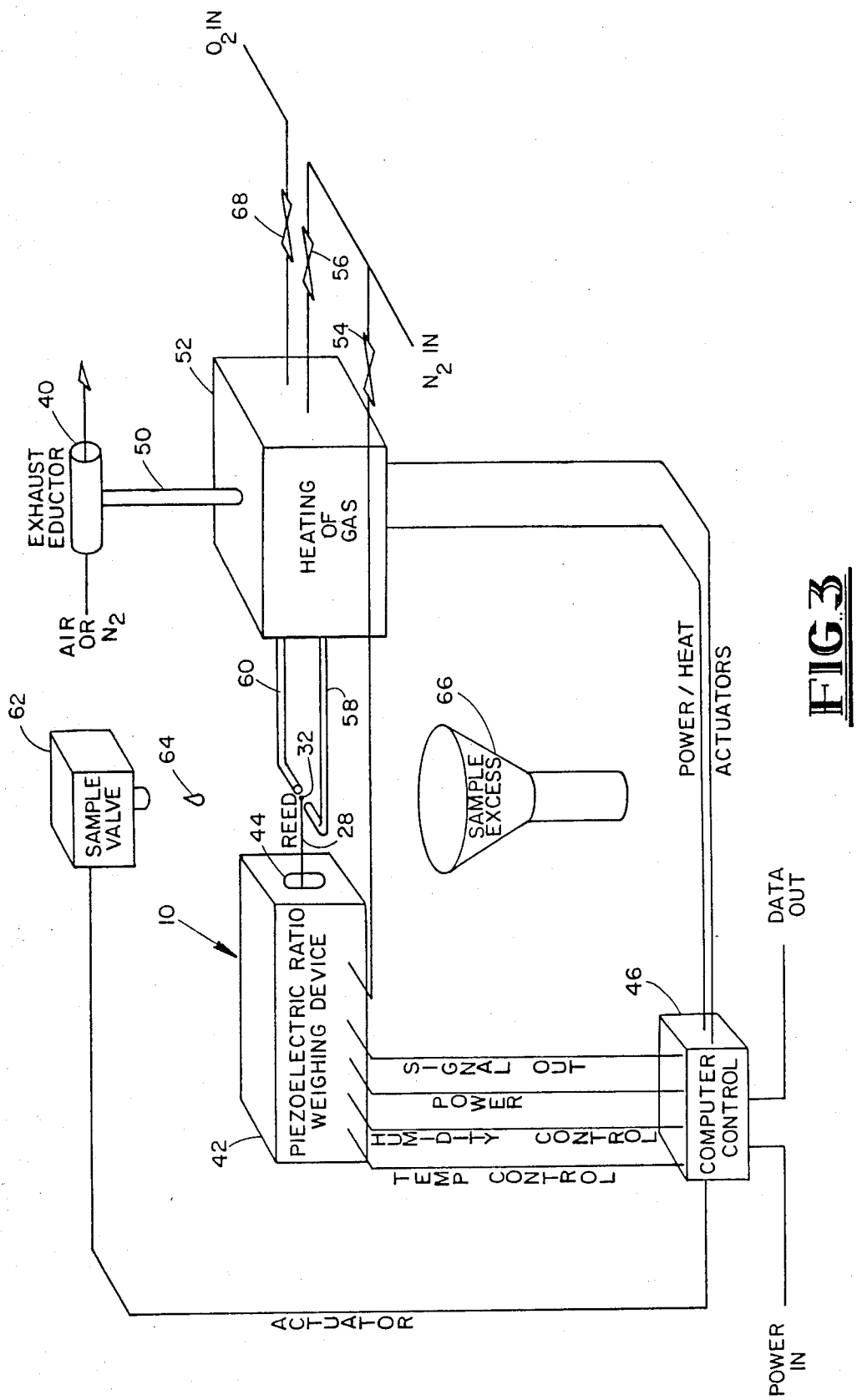
FIG. 3 is a pictorial representation of an automated in-line piezoelectric weight measuring device for use in the petrochemical refining industry.

The entire process as described hereinabove may be automated for an in-line system to determine the carbon residue of petrochemicals as illustrated in FIG. 3. The piezoclectric weighing device 10 is located inside of a container 42 that has a slot 44 in one end thereof. The reed 28 and ball tip 32 extend through slot 44. Because temperature and humidity greatly affect the operation of the piezoelectric weighing device 10 as well as variations in power, a computer control 46 is provided. Computer control 46 provides accurate temperature and humidity control of the container 42 which contains the piezoelectric weighing device 10. Typically the temperature inside of container 42 would be around 125° F. This is slightly hotter than the normal operating temperatures in which the piezoelectric weighing device 10 will be operating. It is easier to provide a constant temperature by heating the container 42 to a known temperature than it would be to refrigerate the container 42. To control humidity, dry nitrogen $N_2$ may be used to continuously purge the container 42. This gives a very accurate humidity control. Also, the computer control 46 provides the regulated AC voltage IN.

In actual operation, the computer control 46 controls everything in a fixed sequence. Either air or nitrogen $N_2$ is turned ON through the exhaust eductor 48, which creates a slight vacuum through conduit 50 in the heating chamber 52. The piezoelectric weighing device 10 inside container 42 is turned ON and zeroed by adjusting the frequency of the AC voltage IN, while dry nitrogen $N_2$ purges the container 42 by the opening of valve 54 by computer control 46. Dry nitrogen continuously purges the container 42 so that temperature and humidity are accurately controlled.

A portion of the dry nitrogen is delivered through valve 56, which is actuated by computer control 46, through heating chamber 52 and conduit 58 to be discharged across ball tip 32 of reed 28. The vacuum created by the exhaust eductor 40 draws the nitrogen from conduit 58, across ball tip 32 of reed 28 through return line 60, heating chamber 52 and conduit 50 to be discharged to atmosphere. Because nitrogen is inert, the flow of nitrogen across ball tip 32 prevents contaminants from interfering with the oxygen sensitive process. Any other type of inert gas could also be used.

Next the sample valve 62 is actuated to cause a drop 64 of the petrochemical being tested to fall and splash on the ball tip 32 of the reed 28. This can occur while the piezoelectric weighing device 10 is either ON or OFF. Any excess of the drop 64 is collected in the sample excess flue 66 located immediately below the ball tip 32 of reed 28. With a portion of the drop 64 clinging to the ball tip 32 of reed 28, the vibratory motion of the reed 28 will sling off any excess. The remainder stays firmly attached to the ball tip 32 due to surface tension. The weight of the sample of the petrochemical being tested is then recorded as an electronic signal by the computer control 46 as will be described in more detail in connection with FIG. 4.

With a signal representing weight of the sample on the ball tip 32 of reed 28 having been determined, temperature of the nitrogen being delivered through conduit 58 across ball tip 32 of reed 28 is increased to approximately 500° C. by the heating chamber 52 as controlled by computer control 46. Within a very short time period (a matter of seconds), excess of the sample other than carbon residue is boiled off of the ball tip 32 of reed 28. This leaves only the carbon residue on the ball tip 32. A signal representing the weight of the carbon residue is again measured and recorded. In a manner as will be described in detail subsequently, the computer control 46 linearizes each of these signals and compares them to the calibrated signal.

To clean the ball tip 32 of the reed 28, valve 56 for the nitrogen is closed and valve 68 to deliver high temperature oxygen enriched air through conduit 58 across the ball tip 32 is opened. The delivering of high temperature oxygen across the ball tip 32 oxidizes any carbon residue. After oxidizing the carbon residue, the carbon residue remaining will flake and fall off ball tip 33, thereby returning the piezoelectric weighing device 10 to the zero point. Thereafter, the process may be repeated. From the computer control 46, data out may be fed to any convenient point to control any portion of an automated system as may be desired. This entire sampling process will take only a matter of seconds or at the most a couple of minutes.

The sampling valve 62 is designed so that it will take a sample from the middle of a processing flow line with the sample valve 62 being purged between samples.

Referring now to FIG. 4, the computer control 46 is explained in more detail. The heart of the computer control 46 is a microprocessor 70. The microprocessor 70 has a display 72 that may be of any conventional type. While a typical cathode ray tube (CRT) may be used, it is envisioned that a more limited display of approximately four lines of forty digits using liquid crystal displays may be used to provide a limited visual indication. It is not necessary that the display 72 have the full display capabilities of a cathode ray tube. The language being used to communicate between the display 32 and the microprocessor 70 would typically be RS-232.

Also connected to the microprocessor 70 is a keyboard 74. Again, while a full-scale keyboard can be used, in the present invention a full-scale keyboard is not necessary. Therefore, the keyboard 74 as is presently envisioned for the current invention may simply be two or three sequencing push buttons that will give the very basic commands to the microprocessor 70. The sequencing push buttons would simply be a subset of the normal full keyboard for a microprocessor.

The microprocessor 70 may also provide an output to an extra terminal 76 or a host computer. The extra terminal 76 receives the same information as received by the display 72.

Referring now to the measuring provided by the computer control 46, the microprocessor 70 provides a digital signal to digital-to-analog converter 78. The digital-to-analog converter 78 converts the digital signal to analog form. The analog signal is then fed to sine wave generator 80. The sine wave generator 80 utilizes energy from a regulated power supply 82 and the analog signal from digital-to-analog converter 78 to give a variable frequency constant amplitude sine wave output. The frequency of the sine wave output may be varied by varying the digital signal from the microprocessor 70. The sine wave output is increased in voltage by step-up transformer 84. The stepped-up sine wave output from step-up transformer 84 is fed to the piezoelectric driver 14.

The sine wave voltage being fed to piezoelectric driver 14 causes the piezoelectric driver to vibrate. By a mechanical linkage 86, the piezoelectric driver 14 causes the piezoelectric receiver 22 to also vibrate. The vibration of the piezoelectric receiver 22 causes an AC voltage output therefrom which is fed to a root means square (RMS) AC to DC converter 88. In the RMS-AC to DC converter 88, the AC signal is converted to a DC signal. The DC signal is fed to a programmable offset gain 90 which receives a feedback loop from the microprocessor 70. By adjustment of the programmable offset gain 90 through the microprocessor 70, a calibration is provided for the range of the total piezoelectric weighing device 10. The programmable offset gain sets the zero point, which is on the leading edge of the resonant frequency for the piezoelectric weighing device 10. The programmable offset gain basically provides the zero point by subtracting the voltage associated with the zero point of operation when no weight is applied to the ball tip 32 of the reed 28 (see FIG. 3).

An output from the programmable offset gain 90 is fed to a programmable gain amplifier 92, which also has a feedback loop with the microprocessor 70. The programmable gain amplifier 92 provides the slope of the curve or what can be referred to as the span over which measurements would be taken. Assume, for example, the system is set to weigh quantities between 0–10 milligrams. By proper adjustment of the programmable gain amplifier 92, weights between 0-10 milligrams will cause the receiver output to be properly scaled on the leading edge of the resonancy frequency curve.

The output from the programmable gain amplifier 92 is fed through an analog-to-digital converter 94 back to the microprocessor 70. Within the microprocessor 70, the signal received from the analog-to-digital converter 94 is linearized by any of a number of methods. If the signal from the analog-to-digital converter 94 can be expressed in a mathematical formula, the microprocessor 70 can automatically convert the signal from the analog-to-digital converter 94 to equalize a certain weight as may be felt on the ball tip 32 of the reed 28. Another possibility is that the microprocessor 70 can contain in memory a chart or plotting of points that can be used to linearize the signal in direct proportion to the weight felt on the ball tip 32 of the reed 28. This provides a very easy means for calibrating the piezoelectric weighing device 10 to known weight standards. Depending on ambient conditions and intended use, the piezoelectric weighing device 10 may need to be calibrated every hour, day, or week.

It should be understood that the microprocessor 70 provides other functions not shown in FIG. 4, but illustrated in FIG. 3, such as temperature and humidity control of the container 42 and the operation of the valves 54, 56 and 68, as well as the heating chamber 52. For simplicity, these have not been illustrated in FIG. 4.

It should be realized that the piezoelectric weighing device 10 as explained in connection with FIG. 1 is only one of many alternative configurations. Referring to FIG. 5, an alternative piezoelectric weighing device 96 is illustrated. The same base 12 as has been previously described will again be utilized. However, the piezoelectric driver 98 is now formed on the same ceramic sheet as the piezoelectric receiver 100 (see FIG. 6). Both the piezoelectric driver 98 and the piezoelectric receiver 100 are formed on a thin metal core 97 by cured ceramic layers 99 on either side thereof. A thin layer of nickel 101 is then deposited on the outside of the cured ceramic layers 99. However, by scoring the surface coating 101 (such as nickel) as represented by score mark 102, the piezoelectric receiver 100 is electrically isolated from the piezoelectric driver 98. Typically, a piezoelectric device will have a thin flat metal core 97 covered on both sides by a doped and cured ceramic 99. A thin layer of nickel 101 is deposited on the outside of the ceramic layers 99. The electrical connections are made to the layers of nickel 101. There may also be a protective coating around the entire device (not shown). Again, the piezoelectric driver 98 as well as the piezoelectric receiver 100 are bonded to, but electrically isolated, from base 12. Input lines 16 and 18 provide for the electrical connection to the piezoelectric driver 98. Likewise, output lines 24 and 26 provide the output signal from the piezoelectric receiver 100.

The reed 28 as well as the ball 32 on the end thereof is connected through a similar type of dielectric material 30 to piezoelectric driver 98. The dielectric material 30 electrically isolates the reed 28 from the piezoelectric driver 98.

The piezoelectric connection as shown in FIG. 1 is sometimes referred to as a series connection and the connection as shown in FIG. 5 is sometimes referred to as a parallel connection. However, the alternative piezoelectric weighing device 96 as shown in FIG. 5 may be used equally as well as the embodiment shown in FIG. 1.

Referring now to FIG. 7, a second alternative piezoelectric weighing device 104 is illustrated. Again a piezoelectric driver 106 is electrically bonded to a base 12 by any suitable means. The piezoelectric driver 106, however, is electrically isolated from base 12. Again, input lines 16 and 18 provide for electrical connections to the piezoelectric driver 106. The reed 28 and the ball tip 32 are connected to one end of the piezoelectric driver 106 by means of the dielectric material 30, which also provides for electrical isolation therefrom. However, in this embodiment, the piezoelectric receiver 108 is bonded on one end to the base 12, but electrically isolated therefrom. The piezoelectric receiver 108 is mechanically connected to piezoelectric driver 106 by means of a sounding post 110. The sounding post 110 electrically isolates the piezoelectric driver 106 from the piezoelectric receiver 108, but transmits the vibratory signals therebetween. The output of the piezoelectric receiver 108 is received through output lines 24 and 26.

Figure 8:
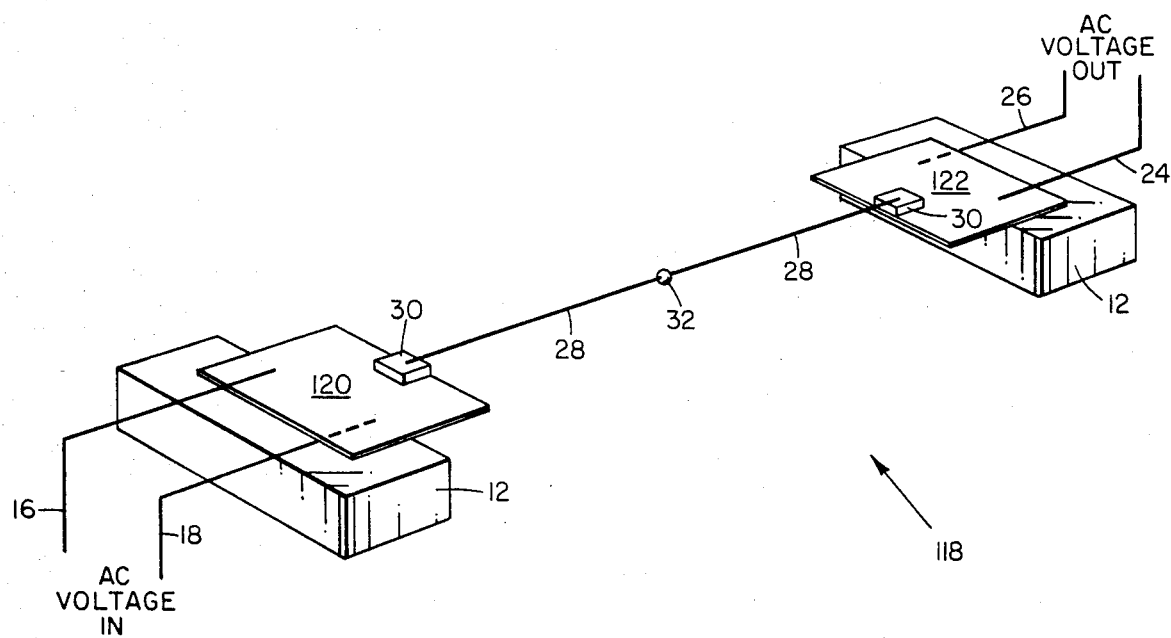
FIG. 8 is a perspective view of yet another alternative piezoelectric weight measuring device.

In FIG. 8, a third embodiment of the piezoelectric weighing device 118 is shown. In this embodiment, reed 28 is fixed on each end to dielectric materials 30, which are, in turn, bonded to piezoelectric driver 120 and piezoelectric receiver 122. Again input lines 16 and 18 provide voltage to piezoelectric driver 120, and output lines 24 and 26 lead away from piezoelectric receiver 122. Piezoelectric driver 120 and piezoelectric receiver 122 are supported by bases 12.

From the above illustration, it should be clear that many different types of configurations for a piezoelectric weighing device can be used and not depart from the scope or spirit of the present invention. Also, it has been determined that many different types of reeds can be used; however, in the preferred embodiment, the reed 28 is a quartz reed with the ball tip 32 being formed on the end thereof. It is preferable that any reed being used have a large length-to-diameter ratio. Flattened rectangular crystals may be substituted for reed 28.

It should also be realized that many different types of control functions can be provided by the computer control 46 with the electronic controls illustrated in FIG. 4 being representative as some of the controls that many be possible. All that is necessary is that (1) the resonant frequency be determined and the system set to operate on the leading edge of the resonant frequency, (2) the zero point be set by the programmable offset gain 90, and (3) the slope of the curve be set by the digital-to-analog converter 78 so that the system continues to operate on the leading edge of the resonant frequency of the system. It should be noted that the system can just as effectively operate when set on the trailing edge of the resonant frequency, but engineers traditionally use the leading edge. The present device can provide an accurate measurement as to the weight of the sample, and, in the petrochemical application discussed, a ratio of the weight of the residue to the weight of the sample.

While the heating chamber 52 of FIG. 3 can be of any particular type, applicant has found that a laser beam would work equally as well. The entire heating chamber 52 could be replaced with a laser that is focused on the ball tip 32 of the reed 28. While an inert gas such as nitrogen flows over the ball tip 32, when heat is desired, the laser would be switched ON by the computer control 46 to provide the heat to either (1) evaporate a part of the sample, or (2) burn off the remainder of the sample. The only problems with the laser arrangement are the cost of the laser and the control of temperature.

There are many other functions that can be performed by the present invention other than determining carbon residue in a petrochemical processing plant. An example could be that the piezoelectric weighing device 10 is used as a humidistat. The ball tip 32 of reed 28 would simply be replaced by a moisture absorbent material. Initially by drying the moisture absorbent material and setting the frequency and offset amplifier 90 so that the piezoelectric weighing device operates on the leading edge of the resonant frequency (at zero condition), thereafter, an atmosphere whose humidity is to be tested can be directed across the moisture absorbent material of the reed 28. The moisture absorbent material would increase in weight dependent upon the humidity of the atmosphere being directed thereacross. This will give a first signal that is representative of weight, which, in turn, represents humidity. Thereafter by comparing this signal to the signal that would be generated by 100% humidity, the particular percent humidity can be determined or scaled by the programmable amplifier 92. Even if the particular signal generated is not a linear signal, the signal can be linearized by a computer so that an output reading that represents the percent humidity is given.

It further should be realized that the piezoelectric weighing device 10 is not dependent upon gravity. Therefore, once a sample is applied to the ball tip 32 of the reed 28, after initial vibrations, the sample remaining is what is being considered. The present device can be used as a type of scale that is suitable for operation in outer space. While gravity may have some effect on the piezoelectric weighing device 10, gravity is not essential to the operation of the device. All that is necessary is that the ball tip 32 of the reed 28 be coated with the liquid being measured.

Also, it may not be necessary to use the reed 28 if a means to apply and remove weight is available. For example, a very sticky substance could be applied directly to the piezoelectric receiver 22 for measuring by vibratory motion. The only problem may be how to remove a portion or all of the sticky substance. All that is necessary for the weight measurement is that the sticky substance effect the resonant frequency of the piezoelectric weighing device 10.

We claim:

1. A device for determining the weight of a first sample comprising:
   a base;
   a piezoelectric driver anchored by a first part thereof to said base;
   means for supplying an AC voltage to said piezoelectric driver to cause a second part of said piezoelectric driver to vibrate upon receiving said AC voltage;
   a piezoelectric receiver mechanically linked to, but electronically isolated from, said piezoelectric driver to transmit vibrations from said piezoelectric driver to said piezoelectric receiver;
   means for applying, directly or indirectly, said first sample to receive said vibrations from said piezoelectric driver, said first sample vibrating with said piezoelectric driver;
   means for receiving output signals from said piezoelectric receiver, said output signals being representative of said vibrations transmitted from said piezoelectric driver;
   frequency of said AC voltage from said supply means being adjusted to set overall operating frequency of said device immediately adjacent one side of a resonant frequency, thereafter said first sample being applied to said applying means to give an output signal from said piezoelectric receiver, comparing said output signal to a calibrated signal to give the absolute weight of said first sample.

2. The device of claim 1 further includes means for heating said first sample to remove a portion thereof from said applying means to form a second sample.

3. The device of claim 1 wherein said applying means includes reed means attached on a first end to receive said vibrations from said piezoelectric driver, said first sample being applied to a second end of said reed means.

4. The device of claim 1 further includes computer means, said computer means supplying said AC voltage and receiving said output signals, said computer means comparing said output signal to said calibrated signal to give said weight.

5. The device of claim 4 wherein said computer means monitors and controls temperature and humidity around said piezoelectric driver and said piezoelectric receiver by drying an enclosed area therearound and regulating temperature therein.

6. The device of claim 5 further includes a source of inert gas, said computer means operating first valve means to discharge said inert gas over said first sample to prevent external influences thereon.

7. The device of claim 6 includes means for heating said inert gas, said computer means heating said inert gas via said heating means after said output signal has been received, said heating of said inert gas removing a portion of said first sample to give a second sample.

8. The device of claim 7 includes a source of oxygen, said computer means operating said first valve means and a second valve means to stop said discharge of said inert gas and to deliver heated oxygen to said second sample to burn said second sample off said reed means.

9. The device of claim 4 wherein said computer means linearizes said output signal with respect to weight.

10. The device of claim 1 wherein said base has dampening means to reduce external vibrations.

11. The device of claim 1 wherein said applying means comprises a reed having first and second ends and a middle portion, said first end being attached to said piezoelectric driver, said second end being attached to said piezoelectric receiver, and said middle portion receiving said first sample.

12. A piezoelectric device for comparing a first signal representing a weight of a control sample with a second signal representing the weight of an unknown sample for determining the absolute weight of said unknown sample, said device comprising:
   a base;
   a piezoelectric driver anchored to, but electrically isolated from, said base;
   a piezoelectric receiver mechanically linked to, but electrically isolated from, said piezoelectric driver to receive vibrations therefrom;
   applying means mechanically linked to said piezoelectric driver to receive vibrations therefrom;
   means for supplying AC voltage to said piezoelectric driver to cause vibrations therein, said supplying means setting frequency of said AC voltage to operate on one side of a slope of resonant frequency of said device;

means for receiving output signals from said piezoelectric receiver as vibrations are received from said piezoelectric driver, a first output signal being generated when said control sample is applied to said applying means, a second output signal being generated when said unknown sample is applied to said applying means, a ratio of said second output signal to said first output signal giving the weight of said unknown sample.

13. The piezoelectric device as recited in claim 12 includes means to linearize said first output signal and said second output signal with respect to weight.

14. The piezoelectric device as recited in claim 12 wherein said setting of frequency of said AC voltage is on a leading edge of said slope of said resonant frequency, said receiving means further including:

offset gain to zero out said output signals from said piezoelectric receiver when no sample is applied to said applying means; and gain amplifier to set gain of said output signals to insure operation on said leading edge when either of said samples is applied to said applying means.

15. The piezoelectric device as recited in claim 14 includes means for maintaining said piezoelectric device at a relatively constant temperature and humidity.

16. The piezoelectric device as recited in claim 15 including means to discharge inert gas over said unknown sample being measured to prevent outside influences thereon, means to heat said inert gas to remove a part of said unknown sample, and means for removing said unknown sample remaining.

17. The piezoelectric device as recited in claim 16 includes sampling valve for applying said unknown sample to said reed from fluid flowing in a conduit.

18. The piezoelectric device as recited in claim 12 wherein a first end of said piezoelectric driver is anchored to said base and a second end of said piezoelectric driver is bonded to a first end of said piezoelectric receiver, a second end of said piezoelectric receiver being bonded to a first end of a reed, a second end of said reed being shaped to receive said samples thereon, said reed being said applying means.

19. The piezoelectric device as recited in claim 12 wherein said piezoelectric driver and piezoelectric receiver are formed from a single ceramic substrate having separate pairs of electrically isolated plates thereon for said piezoelectric driver and said piezoelectric receiver, said single ceramic substrate being bonded on a first end to said base and on a second end to a first end of a reed, a second end of said reed being shaped to receive said samples thereon, said reed being said applying means.

20. The piezoelectric device as recited in claim 12 wherein said piezoelectric driver is anchored on a first end to said base and said piezoelectric receiver is anchored on a first end to said base, soundpost means connected to said piezoelectric driver and said piezoelectric receiver to transmit vibrations therebetween, a reed being attached on a first end to receive said vibrations, a second end of said reed being constructed to receive said samples thereon, said reed being said applying means.

21. The piezoelectric device as recited in claim 12 wherein said applying means has a moisture absorbent portion thereon, said setting of said frequency being when said absorbent portion is dry, said first output signal being when said moisture absorbent portion is saturated with water, and said second output signal is when said saturated condition has been reduced thereby causing said ratio to represent a percent humidity.

22. The device of claim 12 wherein said applying means comprises a reed having first and second ends and a middle portion, said first end being attached to said piezoelectric driver, said second end being attached to said piezoelectric receiver, and said middle portion receiving said samples.

23. A method of determining the weight of a small sample using a piezoelectric device consisting of the following steps:

(a) vibrating a piezoelectric driver that is mechanically linked to, but electrically isolated from, a piezoelectric receiver and means for applying said small sample by supplying an AC voltage thereto;

(b) setting said AC voltage so that said piezoelectric drive, piezoelectric receiver, and applying means in combination operate on one side of their combined resonant frequency;

(c) first applying a control sample to said applying means which slightly shifts said resonant frequency;

(d) first recording a first output signal from said piezoelectric receiver;

(e) first removing said control sample;

(f) second applying said small sample to said applying means;

(g) second recording a second output signal from said piezoelectric receiver; and (h) comparing said second signal with said first signal to give the weight of said small sample.

24. The method as recited in claim 23 includes after said comparing step a step of second removing said small sample, and repeating steps (a), (f), (g), and (h) for subsequent small samples.

25. The method as recited in claim 24 includes a continuous step of maintaining constant temperature and humidity around said piezoelectric receiver.

26. The method as recited in claim 25 wherein said second applying step includes actuating a sampling valve to obtain said small sample from a fluid flowing in a conduit.

27. The method as recited in claim 24 includes after said setting step a step of discharging an inert gas over said small sample applied to said applying means to prevent outside influences on said small sample, said second removing step includes heating said small sample to vaporize a portion thereof with vapors being removed by said inert gas, said applying means being a reed attached on a first end to said piezoelectric receiver and said small sample on a second end of said reed.

28. The method as recited in claim 27 includes a third removing step of applying heated oxygen to said small sample remaining to burn off said small sample remaining.

29. The method as recited in claim 23 includes a step of linearizing said first signal and said second signal with respect to weight of said control sample and said small sample, respectively.

30. The method as recited in claim 29 includes after said setting step a step of adjusting offset gain to zero output signals from said piezoelectric receiver when no sample is applied to said reed means, and varying gain of said output signal to control span of weights of said small samples in which said weight can be determined.

31. The method as recited in claim 30 includes mechanically isolating said piezoelectric driver, piezoelectric receiver, and reed means from external vibrations.

32. The method as recited in claim 23 wherein said applying means comprises a reed having first and second ends and a middle portion, said first end being attached to said piezoelectric driver, said second end being attached to said piezoelectric receiver, and said middle portion receiving said samples.

33. An apparatus for determining carbon residue in a petroleum product comprising:
 a base;
 a piezoelectric driver with a first part being bonded to, but electrically isolated from, said base;
 a piezoelectric receiver being mechanically linked to, but electrically isolated from, said piezoelectric driver to transmit vibrations therebetween;
 a reed being mechanically linked on a first end to either said piezoelectric driver or said piezoelectric receiver to transmit vibrations therebetween;
 generating means for applying an AC voltage to said piezoelectric driver to cause vibrations therein, said generating means setting frequency of said AC voltage to operate on a leading edge of a resonant frequency for said apparatus;
 means for applying a small sample of said petroleum product to a second end of said reed, said small sample causing said resonant frequency of said apparatus to shift toward said frequency of said AC voltage, said piezoelectric receiver giving a first output signal with said small sample applied to said reed;
 means for heating said small sample to evaporate essentially everything except carbon residue therein, said piezoelectric receiver giving a second output signal with said carbon residue on said reed; and
 means for calibrating said output signals to determine absolute weights of said small sample and said carbon residue.

34. The apparatus as recited in claim 33 includes control means, said control means operating said generating means, applying means, heating means, and calibrating means.

35. The apparatus as recited in claim 34 wherein said control means includes means to linearize said first output signal and said second output signal with respect to weight.

36. The apparatus as recited in claim 35 wherein said control means includes offset gain means to zero output signals from said piezoelectric receiver when no sample is applied to said reed and gain means for said output signals to set scaling of output to A/D converter over which measurements are to be taken to control range of weights of said small sample that can be measured.

37. The apparatus as recited in claim 36 wherein said control means includes a microprocessor with input means and display means connected thereto.

38. The apparatus as recited in claim 34 wherein said control means maintains a relatively constant humidity and temperature around said piezoelectric receiver and said piezoelectric driver.

39. The apparatus as recited in claim 38 wherein said control means operates first valve means to discharge an inert gas over said small sample to prevent outside influences thereon.

40. The apparatus as recited in claim 39 wherein said control means actuates heater means for heating said inert gas to cause said evaporation, said control means operating said first valve means to stop discharge of said inert gas over said small sample and to begin discharge of heated air or oxygen over said small sample to burn up said carbon residue on said second end of said reed by actuating second valve means.

41. The apparatus as recited in claim 33 wherein said applying means includes a sampling valve located in a fluid flow line of said petroleum product, said sampling valve actuating to deliver said small sample to said second end of said reed.

* * * * *

UNITED STATES PATENT AND TRADEMARK OFFICE
CERTIFICATE OF CORRECTION

PATENT NO. : 4,697,657
DATED : October 6, 1987
INVENTOR(S) : Joe L. Portman, Jr., et. al.

It is certified that error appears in the above-indentified patent and that said Letters Patent is hereby corrected as shown below:

On the Title page, item [73], Assignee: should be --"Alcor, Inc., San Antonio, Texas"--.

Signed and Sealed this

Seventh Day of June, 1994

Attest:

BRUCE LEHMAN

Attesting Officer    Commissioner of Patents and Trademarks